US00PP12649P2

(12) United States Plant Patent
Hayashi

(10) Patent No.: US PP12,649 P2
(45) Date of Patent: May 28, 2002

(54) ANTHURIUM PLANT NAMED 'MELODY'

(76) Inventor: Calvin Hayashi, 15-1480 B Nanawale Homestead Rd., P.O. Box 242, Pahoa, HI (US) 96778

( * ) Notice: Subject to any disclaimer, the term of this patent is extended or adjusted under 35 U.S.C. 154(b) by 0 days.

(21) Appl. No.: 09/429,638

(22) Filed: Oct. 29, 1999

(51) Int. Cl.[7] ..... A01H 5/00
(52) U.S. Cl. ..... Plt./365

(58) Field of Search ..... Plt./365, 367

*Primary Examiner*—Bruce R. Campell
*Assistant Examiner*—June Hwu
(74) *Attorney, Agent, or Firm*—Banner & Witcoff, Ltd.

(57) ABSTRACT

The new Anthurium cultivar named 'Melody' is characterized by its pink, generally heart-shaped spathe, with an indentation along one edge, and long, straight peduncles which carry and position the spathe well above the green leaves. The new cultivar is rapidly growing and is well-suited for cut flower production as well as for a potted plant.

2 Drawing Sheets

The present invention comprises a new and distinct cultivar of anthurium, botanically known as *Anthurium andraeanum*, and hereinafter referred to by the cultivar name 'Melody.'. This new cultivar is a product of a planned breeding program, and was created from a cross made during such a program in Pahoa, Hi., U.S.A. The female, or seed parent, was a unnamed red seedling (RHS45B) and the male, or pollen plant, was 'Midori' (RHS 135B) (unpatented). 'Melody' was discovered and selected as a flowering plant within the progeny of the stated cross by Calvin K. Hayashi in a controlled growing environment in Pahoa, Hi., U.S.A. Subsequent asexual reproduction in greenhouse conditions, by stem cutting has demonstrated that the combination of characteristics as herein disclosed for the new cultivar are firmly fixed and are retained through successive generations of asexual reproduction.

SUMMARY OF THE INVENTION

The following traits have been repeatedly observed in mature plants in greenhouse conditions of approximately 85° F., 75% humidity, and 80% shade, which in combination distinguish 'Melody' as a new and distinct cultivar.

'Melody' grows at a rate of approximately 18 inches per year, reaching its mature size of approximately 22 inches in approximately 1½ years.

The spathe or blossoms are pink (RHS 51A) with a length of 7 inches and a width of 5½ inches.

The shape of the spathe is generally heart-shaped, with one edge slightly indented.

The peduncle is straight and strong, and the spathes stand above the leaves.

The leaves are relatively large and green in color. New leaves grow approximately 22 inches in overall height when grown to maturity in a 10-inch plastic container.

The spadix is approximately 2⅞ inches long, 1⅜ inches in circumference, having a generally yellow-green color at early growth stages and maturing into an ivory color at maturity.

The plant flowers continuously. When first flowering, the spathes are small in size, becoming larger with each successive blossom as the plant matures in growth.

BRIEF DESCRIPTION OF THE DRAWINGS

The accompanying photographs show a typical specimen of the new cultivar 'Melody' with the colors being as true as possible with illustrations of this type.

FIG. 1 is a frontal perspective view of the entire plant.

FIG. 2 is a close up view of a typical spathe.

DETAILED BOTANICAL DESCRIPTION

The following observations, measurements, and values describe the plant grown in Pahoa, Hi., U.S.A., under greenhouse conditions of approximately 85° F., 75% humidity, and 80% shade, which closely approximate those generally used in horticulture practice. Color references are made to The R.H.S. Colour Chart of The Royal Horticulture Society.

Botanical classification: *Anthurium andraeanum*, cultivar name, 'Melody'.

Parentage:
- *Male parent.*—*Anthurium andraeanum* 'Midori'.
- *Female parent.*—*Anthurium andraeanum* unnamed red seedling.

Propagation: At the present time, propagation is by stem cutting. Tissue culture (in vitro) is most likely possible with this cultivar.

Plant: When grown in a 10-inch plastic container, the plant is approximately 34 inches in overall height and approximately 24 inches in width.

Leaves:
- *Size.*—Approximately 15½ inches in length and 9¾ inches in width.
- *Texture.*—Coriaceous.
- *Apex.*—Acuminate.
- *Leaf shape.*—Ovate.
- *Venation.*—Pinnate.
- *Base shape.*—Cordate.
- *Margin.*—Entire.
- *Color.*—Upper side RHS 137A, under side RHS 137C.
- *Petiole.*—Color, RHS 137C; length 22 inches; texture, smooth.

Flowers:
- *Buds.*—The spathe is rolled around the spadix; after opening, the spathe stands above the leaves by approximately 10 inches.

Spathe (blossom):

*Size*.—Approximately 7 inches in length and 5½ inches in width.

*Color*.—Upper side, RHS 51A; under side, RHS 51C.

*Arrangement*.—The spathes stand on long, straight peduncles and are set at an angle approximately 75 degrees to the peduncles. The color designation of the peduncle in RHS 178B.

*Apex shape*.—Cuspidate.

*Base shape*.—Cordate.

*Venation*.—Pinnate.

*Margin*.—Entire.

*Texture*.—Coriaceous.

*Inflorescence*.—On plant, twelve to sixteen weeks. Cut flower, six to eight weeks.

*Flower production*.—Approximately six flowers per year.

Reproductive organs:

*Spadix*.—Immature stage, RHS 144B; mature stage, RHS 155B.

*Stamens*.—There are four stamens surrounding the pistil. The stamens are visible only when they are separated from the individual reproductive organs from the main axil. The stamen size is approximately 1/16 inch. The stamen color is RHS 155B.

*Anthers and filaments*.—Not clearly visible.

*Pollen*.—RHS 155D in color.

*Pistils*.—Grown firmly together with the pulpy main axil and sitting between the stamens. The color is RHS 144B in immature stage and matures to RHS 155B. It is shaped approximately square and approximately 1/16 inch.

*Seeds*.—Seeds are oval. Immature seeds are RHS 141A. Mature seeds are RHS 12A.

Roots: New growth is pulpy and pink in color, with the very tips being light yellow. Older roots are generally brownish-grey.

Disease resistance: Through observation to date, 'Melody' exhibits good tolerance to anthracnose.

General observations: 'Melody' is a relatively rapid growing anthurium, which under optimum growing conditions produces approximately six blossoms per year. *Anthurium adraeanum* varieties are generally grown in tropical or sub-tropical climates with temperatures ranging between 60° to 90° F. At earlier stages of growth, the plant produces smaller blooms. Each successive bloom becomes larger as the plant matures. The spathes are held on long, straight peduncles reaching lengths of 32 inches. Because of its good blooming habit and coloration, this new and distinct cultivar is well suited for cut flower production as well as for a plotted plant. Due to this unique combination of characteristics, 'Melody' provides a valuable new cultivar of *Anthurium andraeanum*.

I claim:

1. A new and distinct cultivar of *Anthurium andraeanum* named 'Melody,' as illustrated and described.

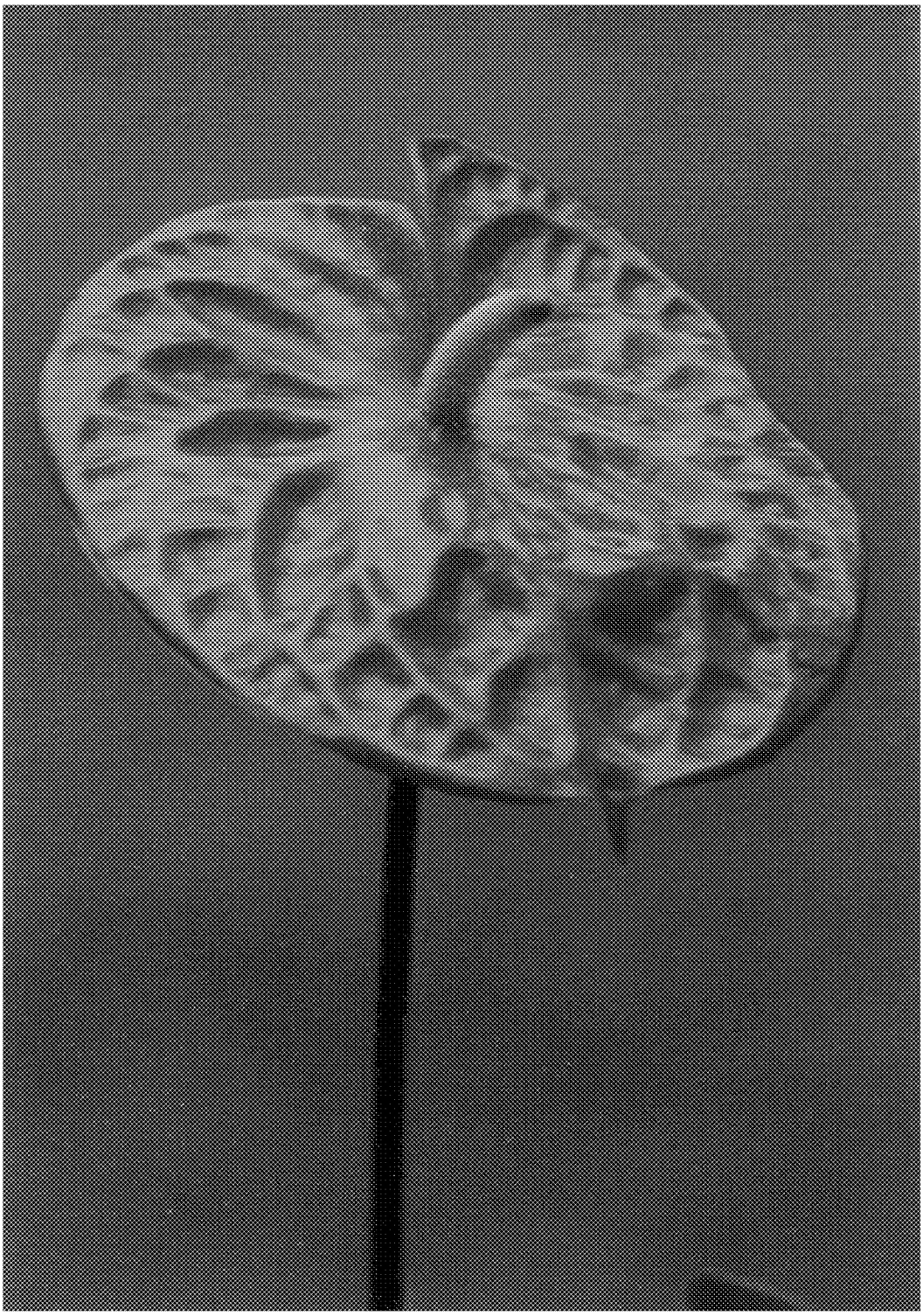

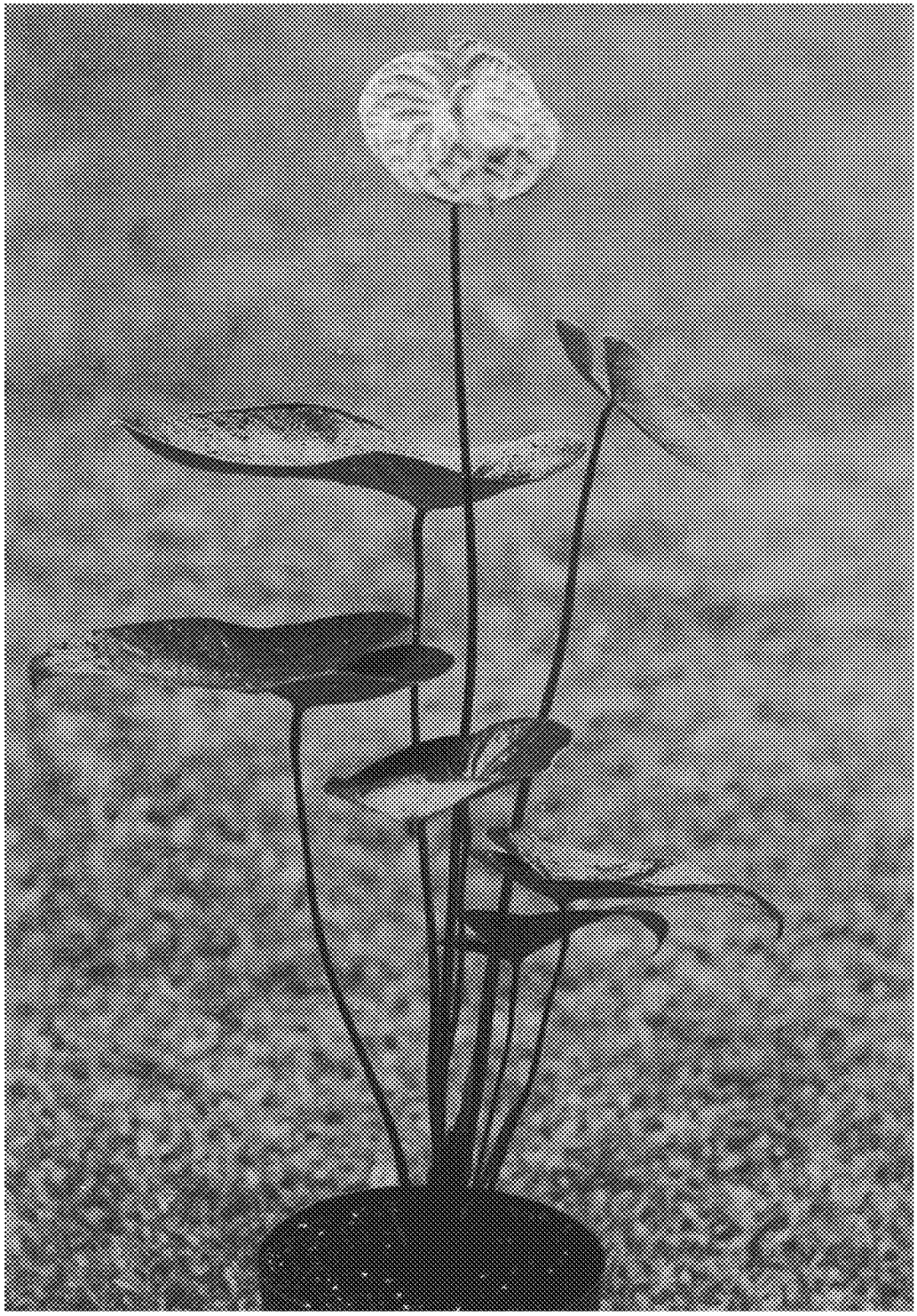

* * * * *